US010426515B2

(12) United States Patent
Shivkumar

(10) Patent No.: US 10,426,515 B2
(45) Date of Patent: Oct. 1, 2019

(54) TRANSSEPTAL ACCESS DEVICE AND METHODS

(71) Applicant: The Regents of the University of California, Oakland, CA (US)

(72) Inventor: Kalyanam Shivkumar, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 389 days.

(21) Appl. No.: 14/581,388

(22) Filed: Dec. 23, 2014

(65) Prior Publication Data

US 2015/0182255 A1   Jul. 2, 2015

Related U.S. Application Data

(60) Provisional application No. 61/920,912, filed on Dec. 26, 2013.

(51) Int. Cl.
*A61B 17/34* (2006.01)
*A61B 17/00* (2006.01)

(52) U.S. Cl.
CPC ...... *A61B 17/3478* (2013.01); *A61B 17/3415* (2013.01); *A61B 2017/00243* (2013.01)

(58) Field of Classification Search
CPC .......... A61B 17/0057; A61B 17/06109; A61B 17/12; A61B 17/3478; A61B 17/3415; A61B 2017/00243; A61B 17/12136
USPC ...................................................... 606/185
See application file for complete search history.

(56) References Cited

U.S. PATENT DOCUMENTS

| 5,876,399 A * | 3/1999 | Chia ................. A61B 18/1492 600/374 |
| 7,450,999 B1 * | 11/2008 | Karicherla ......... A61B 5/02152 607/126 |
| 2007/0203391 A1 * | 8/2007 | Bloom ............. A61B 17/00234 600/37 |
| 2008/0039897 A1 * | 2/2008 | Kluge ................. A61B 5/0215 607/17 |
| 2013/0046305 A1 * | 2/2013 | Davies .............. A61B 18/1492 606/45 |
| 2013/0204175 A1 * | 8/2013 | Sugimoto ........... A61M 27/002 604/8 |
| 2014/0012181 A1 * | 1/2014 | Sugimoto ........... A61M 27/002 604/9 |

OTHER PUBLICATIONS

Horstkotte et al., "Death due to transprosthetic catheterization of a Björk-Shiley prosthesis in the aortic position," 1986, Am J Cardiol, 58: 566-567.

(Continued)

*Primary Examiner* — Diane D Yabut
*Assistant Examiner* — Majid Jamialahmadi
(74) *Attorney, Agent, or Firm* — Riverside Law, LLP

(57) ABSTRACT

The present invention relates to systems and methods for accessing the left heart of a subject. For example, the invention includes a percutaneous inter-ventricular transseptal technique for accessing the left ventricle. In certain embodiments, the invention includes guiding a transseptal sheath to the right ventricle and positioning the transseptal sheath within the inter-ventricular septum.

10 Claims, 5 Drawing Sheets

SUPERIOR APPROACH (via SVC)

(56) References Cited

OTHER PUBLICATIONS

Pluta et al., "Transseptal versus transaortic approach for radiofrequency ablation in patients with cardioverter-defibrillator and electrical storm," 2010, J Interv Card Electrophysiol, 28: 45-50.
Herweg et al., 2010, "Ablation of Left Ventricular Tachycardia via Transeptal Approach and Crossing of a Mechanical Mitral Valve Prosthesis," Pacing Clin Electrophysiol, 33: 900-903.
Rigaud et al., "Retrograde catheterization of left ventricle through mechanical aortic prostheses," 1987, Eur Heart J, 8: 689-696.
Kiefer et al., 2013, "Invasive Hemodynamic Evaluation in Patients With Mechanical Aortic Valves," Catheter Cardiovasc Inter, 82(1): 43-50.
Morgan et al., "Left Heart Catheterization by Direct Ventricular Puncture: Withstanding the Test of Time," 1989, Cathet Cardiovasc Diagn, 16: 87-90.
Liu et al., "The transventricular-transseptal access to the aortic root: a new route for extrapleural trans-catheter aortic stent-valve implantation," 2011, Eur J Cardiothorac Surg, 39: 635-641.

* cited by examiner

TRANSSEPTAL ACCESS DEVICE AND METHODS

CROSS-REFERENCE TO RELATED APPLICATIONS

This application claims priority to U.S. Provisional Patent Application No. 61/920,912 filed Dec. 26, 2013, the contents of which are incorporated by reference herein in their entirety.

STATEMENT REGARDING FEDERALLY SPONSORED RESEARCH OR DEVELOPMENT

This invention was made with government support under R01HL084261, awarded by the National Institutes of Health (NIH). The government has certain rights in the invention.

BACKGROUND OF THE INVENTION

Catheter ablation of ventricular tachycardia (VT) is typically performed using either the atrial transseptal approach or a retrograde aortic approach in order to gain access to the left ventricle (LV). However, neither approach is feasible in the setting of mechanical aortic and mitral valve replacements, given the risk of catheter entrapment and death (Horstkotte et al., 1986; Am J Cardiol, 58: 566-567; Kober et al., 1987, Cathet Cardiovasc Diag, 13: 262-265). Therefore, approaches that avoid traversing these valves, such as a percutaneous trans-apical approach, have been developed (Lichtenstein et al., 2006, Circulation, 114: 591-596; Lim et al., 2008, Catheter Cardiovasc Interv, 71: 915-918; Mosca et al., 1995, J Thorac Cardiovasc Surg, 109: 147-154; Pluta et al., 2010, J Intery Card Electrophysiol, 28: 45-50). However, the trans-apical approach is associated with a significant rate of access related complications, particularly bleeding at the puncture site, and necessitates the placement of closure devices in the LV (Brown et al., 2009, Catheter Cardiovasc Interv, 74: 137-142; Pitta et al., 2010, Catheter Cardiovasc Interv, 76: 993-997).

Thus, there is a need in the art for safe and effective methods of accessing the left ventricle in subjects in need. The present invention satisfies this unmet need.

SUMMARY OF THE INVENTION

The present invention provides a method of providing access to the left heart of a subject. The method comprises inserting a puncture needle and transseptal access sheath into the vasculature of the subject; advancing the puncture needle and transseptal access sheath into the right ventricle; guiding the puncture needle and transseptal access sheath to the inter-ventricular septum; advancing the puncture needle through the inter-ventricular septum into the left ventricle; and advancing the transseptal access sheath over the puncture needle.

In one embodiment, the puncture needle and transseptal access sheath are advanced into the right ventricle via the superior vena cava. In one embodiment, the puncture needle and transseptal access sheath are advanced into the right ventricle via the inferior vena cava. In one embodiment, the puncture needle and transseptal access sheath are advanced into the right ventricle within a primary sheath guided to the right ventricle.

In one embodiment, the method comprises determining a location on the inter-ventricular septum where the puncture needle and transseptal access sheath is to be guided. In one embodiment, determining the location on the inter-ventricular septum comprises the use of real-time fluoroscopy, coronary angiography, Intracardiac echocardiography (ICE), or combination thereof.

In one embodiment, the method is used to guide one or more instruments selected from the group consisting of therapeutic catheters, imaging catheters, probes, and surgical instrumentation, into the left heart.

In one embodiment, the method is used to allow access for the treatment of a condition or defect in the left heart. In one embodiment, the method is used to allow access for the diagnosis a condition or defect in the left heart. In one embodiment, the method is used to guide an ablation catheter into the left heart for treatment of ventricular tachycardia.

The present invention provides a system for providing access to the left heart of a subject. The system comprises a transseptal sheath having an inner lumen and a puncture needle, wherein the transseptal sheath is capable of being positioned in the inter-ventricular septum to provide a passageway between the right ventricle and the left ventricle.

In one embodiment, the system further comprises a primary sheath. In one embodiment, system further comprises a guidewire. In one embodiment, the transseptal sheath comprises a dilator. In one embodiment, the transseptal access sheath and puncture needle are integrated into a specialized catheter device.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Definitions

Figure 1:
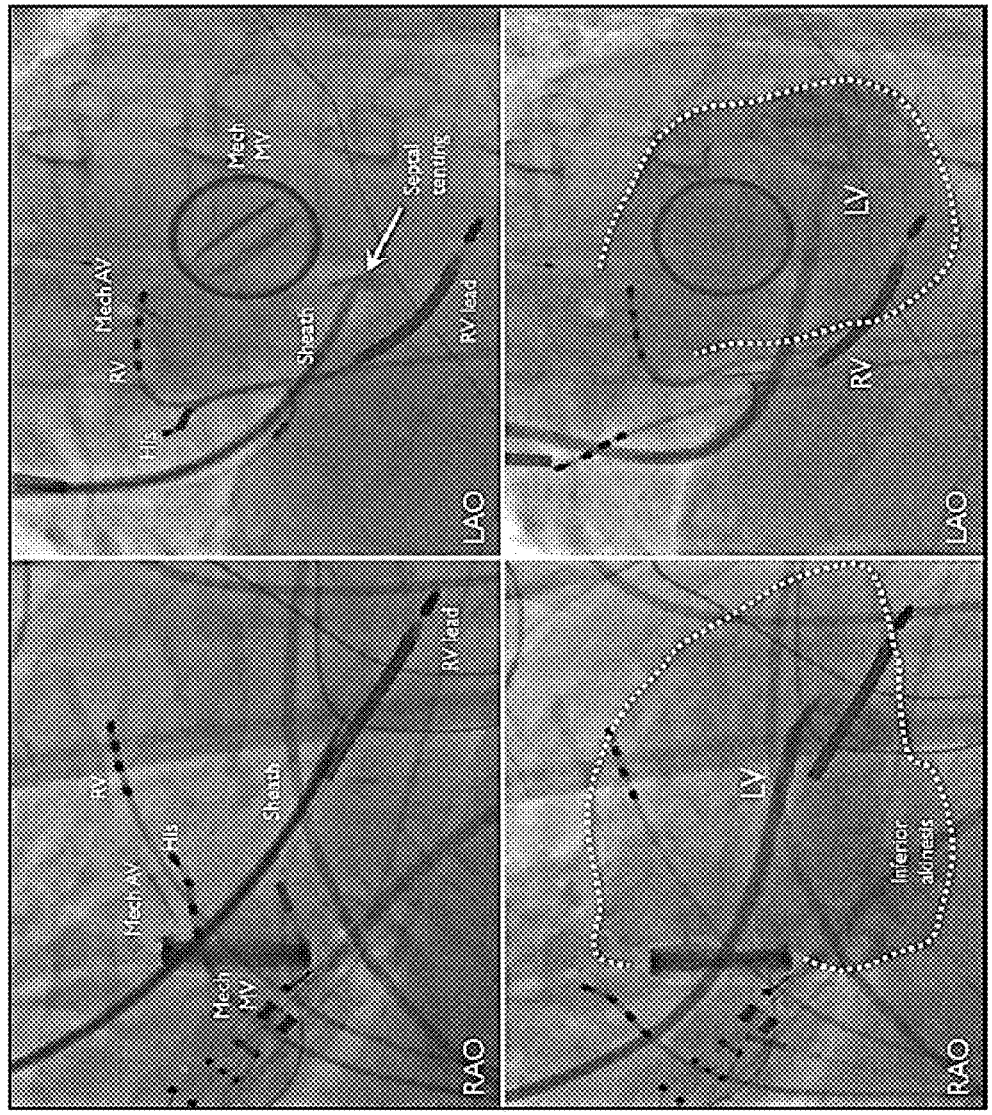
FIG. 1 is a set of images depicting the inter-ventriclar setpal puncture technique. Upper right panel shows the transseptal needle that has been advanced through a Mullins transseptal sheath via the right internal jugular vein and positioned above the ICD coil, at the muscular inter-ventricular septum. Staining of the inter-ventricular septum, best seen in the LAO view, is performed to confirm position. The needle is advanced across the septum and the sheath and dilator are advanced over the needle. The needle and dilator are removed and angiography of the LV is performed to assess position of the sheath in the LV (lower panels). RAO=right anterior oblique view, LAO=left anterior oblique view, RV=right ventricular catheter, His=Bundle of His catheter, LV=left ventricle, Mech MV=mechanical mitral valve, Mech AV=mechanical aortic valve.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to make, use, or perform the disclosed invention.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention includes a device, system, and method for providing access to the left heart of a subject. For example, in certain embodiments, the method of the invention comprises percutaneous inter-ventricular transseptal access to the left ventricle. In one embodiment, the invention comprises a vascular access route, wherein one or more components are delivered to the heart via the vasculature. The invention is based in part upon the discovery that inter-ventricular transseptal access to the left ventricle is efficient and safe, as it produces little to no bleeding. Further it is found that the inter-ventricular transseptal access site exhibits spontaneous closure, thereby eliminating the need for closure of the puncture access site. Described herein is the percutaneous inter-ventricular transseptal puncture technique and placement of a sheath across the inter-ventricular septum. This method allowed for stable left heart access and spontaneous closure of the septal access site.

The present invention allows for the delivery of catheters, probes, surgical equipment, instrumentation, and the like. The invention may be used for any procedure performed in the left heart, including in the left atrium, left ventricle, mitral valve, and aortic valve. For example, the invention may be used for any procedure in the fields of cardiology, cardiac surgery, cardiac electrophysiology, and the like. The device, system, and method of the invention may be used on any subject in need, but may be particularly useful in subjects where surgical or arterial access via the aortic and/or mitral valves is dangerous. For example, the present invention allows for safe access to the left heart in patients having mechanical valve prosthetics which makes traditional arterial access dangerous.

In one embodiment, the invention allows for the delivery of a therapeutic catheter/probe to the left heart in order to provide a treatment or therapy of a disease or tissue defect. In one embodiment, the invention allows for the delivery of an ablation catheter for the treatment of VT. In another embodiment, the invention allows for the delivery of a therapeutic agent, for example, a drug, small molecule, peptide, nucleic acid, or the like, to the left heart. In another embodiment, the invention allows for the delivery of an imaging catheter, including, but not limited to, ultrasound and fiberoptic catheters, to the left heart.

In one embodiment, the invention includes a system for inter-ventricular transseptal access to the left heart. For example, in certain embodiments, the system of the invention comprises a specialized catheter that provides access to the left heart from the right ventricle. In one embodiment, the system comprises a transseptal access sheath that is positioned through the inter-ventricular septum, thereby creating a passageway between the right ventricle and left ventricle. In one embodiment, the transseptal access sheath is integrated with a primary sheath, dilator, puncture needle, catheter, or combination thereof. For example, in one embodiment, the system of the invention comprises a transseptal access module as an integrated component within a primary sheath. In certain embodiments, the transseptal access module is disposable. In another embodiment, the transseptal access sheath is used in conjunction with a sheath, dilator, puncture needle, or catheter known in the art. In one embodiment, the transseptal access sheath comprises an inner lumen, which allows the passage of catheters and instrumentation from the right ventricle to the left ventricle. In one embodiment, the outer diameter of the transseptal access sheath is about 6 Fr to about 32 Fr or more. In one embodiment, the inner diameter of the transseptal access sheath is about 6 Fr to about 32 Fr or more.

The present invention includes a method of providing percutaneous inter-ventrical transseptal access to the left heart. For example, it is described herein that puncture of the inter-ventricular septum and the insertion of a sheath from the right ventricle to the left ventricle, through the inter-ventricular septum, is a safe and effective method of accessing the left ventricle and the rest of the left heart. The method may be used for any therapeutic, diagnostic, or interventional method known in the art. For example, the method may be used for the treatment or diagnosis of VT or the delivery of biologicals, cells, small molecules, or percutaneous hemodynamic assist cannulas.

The method described herein may be used in any subject in need of a procedure requiring access to the left heart. In certain embodiments, the method is used in a subject where traditional access to the left heart is difficult or dangerous.

Traditionally, LV diagnostic hemodynamic monitoring and electrophysiological procedures in patients with combined mechanical aortic and mitral valve replacements have presented a challenge. In one patient, crossing of a mechanical mitral valve was reported for VT ablation in the setting of a LV assist device (Herweg et al., 2010, Pacing Clin Electrophysiol, 33: 900-903). The risks of catheter entrapment, hypotension, life-threatening valvular insufficiency, and death have shown that crossing these valves is undesirable (Horstkotte, et al., 1986, Am J Cardiol, 58: 566-567; Kober et al., 1987, Cathet Cardiovas Diagn, 13: 262-265; Rigaud et al., 1987, Eur Heart J, 8: 689-696; Robles et al., 1977, Chest, 72: 98-99). Coronary pressure sensing wires have been used for invasive hemodynamic evaluation and measurement of bileaflet mechanical valve gradients (Kiefer et al., 2013, Catheter Cardiovasc Inter). However, these techniques are not suitable when larger catheters are needed to be introduced into the LV. Therefore, a percutaneous trans-apical approach has been undertaken for electrophysiology and interventional procedures in the LV. This method has been used for over 50 years for measuring gradients across aortic valve prostheses (Levy et al., 1964, N Engl J Med, 271: 273-280; Wong et al., 1981, 7: 425-432). Hsieh et al. described catheter ablation of VT using this technique (Hsieh et al., 2010, Circ Arrhythm Electrophysiol, 2010, 3: 178-185). However, trans-apical approaches carry a high risk of bleeding and other major and minor complications, ranging from 8 to 40%. These risks include pericardial bleeding, pneumothorax, hypotension, and injury to intercostal vessels or coronary arteries (Lim et al., 2008, Catheter Cardiovasc Interv, 71: 915-918; Brown et al., 2009, Catheter Cardiovasc Interv, 74: 137-142; Pitta et al., 2010, Catheter Cardiovasc Interv, 76: 993-997; Morgan et al., 1989, Cathet Cardiovasc Diagn, 16: 87-90; Ommen et al., 1998, Cathet Cardiovasc Diagn, 44: 175-178; Semple et al., 1968, Br Heart J, 30: 402-406; Walters et al., 2003, Catheter Cardiovasc Interv, 58: 539-544). Further, the trans-apical approach requires the closure of the apical access site given the high risk of bleeding (Nietlispach et al., 2012, Can J Cardiol, 28: e515-517).

Trans-ventricular delivery of large devices into the left ventricle from the right ventricle free wall using a subxiphoid approach across the inter-ventricular septum has been described in porcine hearts, where this procedure was performed successfully under magnetic resonance or echocardiographic guidance (Halabi et al., 2013, J Cardiovasc Magn Reson, 15: 10; Liu et al., 2011, Eur J Cardiothorac Surg, 39: 635-641). However, crossing the right ventricle and inter-ventricular septum can increase the complication rate of either procedure alone and would still require the need for epicardial access and closure of the right ventricle free wall. In contrast, the present invention describes a safe and effective percutaneous access method that, in certain instances, does not necessitate closure.

In one embodiment, the method comprises performing one or more standard procedures to evaluate or monitor the anatomy and function of the heart of the subject. Exemplary procedures include, but are not limited to, cardiac CT angiography, echocardiography, ventriculography, levophase imaging, electrocardiography, percutaneous cardiac assist, and the like. Such procedures may be conducted prior to, during, or after, advancement of a catheter or puncture device to the right ventricle of the subject. For example, one or more procedures may be performed to evaluate the cardiac rhythm; to evaluate cardiac function; to evaluate the anatomy of the right ventricle, left ventricle, and/or inter-ventricular septum; to identify tissue defects; or to identify the location of blood vessels that should be avoided during puncture.

In certain embodiments, the method comprises delivery of one or more agents to the subject as appropriate during standard cardiac procedures. For example, the method comprises delivery of general or local anesthesia and anticoagulants. In one embodiment, the method comprises delivery of an anticoagulant to maintain an average clotting time above about 250 seconds.

The method described herein comprises a percutaneous approach to access the right ventricle and inter-ventricular septum. As such, in one embodiment, the method comprises guiding a puncture device and/or transseptal access sheath to the right ventricle. Guiding of the puncture device and transseptal access sheath to the right ventricle may be done in any standard method known in the art. For example, in one embodiment, the method comprises guiding a guidewire to the right ventricle and advancing a sheath over the guidewire. In certain embodiments, the method comprises accessing the right ventricle and inter-ventricular septum through the vasculature of the subject. That is, in certain embodiments, the invention comprises a percutaneous transvascular approach.

Figure 4:
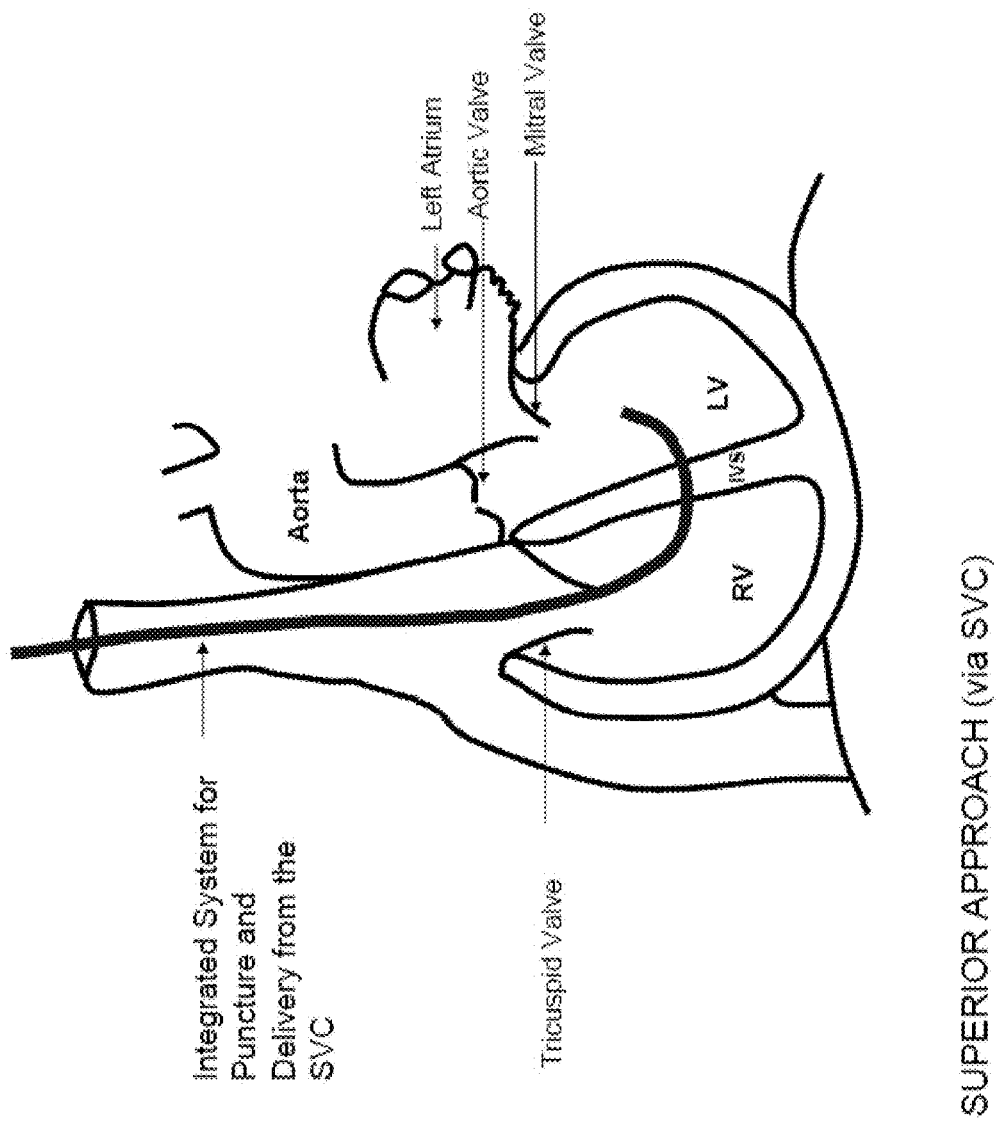
FIG. 4 is a schematic depicting the inter-ventricular transseptal access technique using a superior approach via the superior vena cava (SVC).
Figure 5:
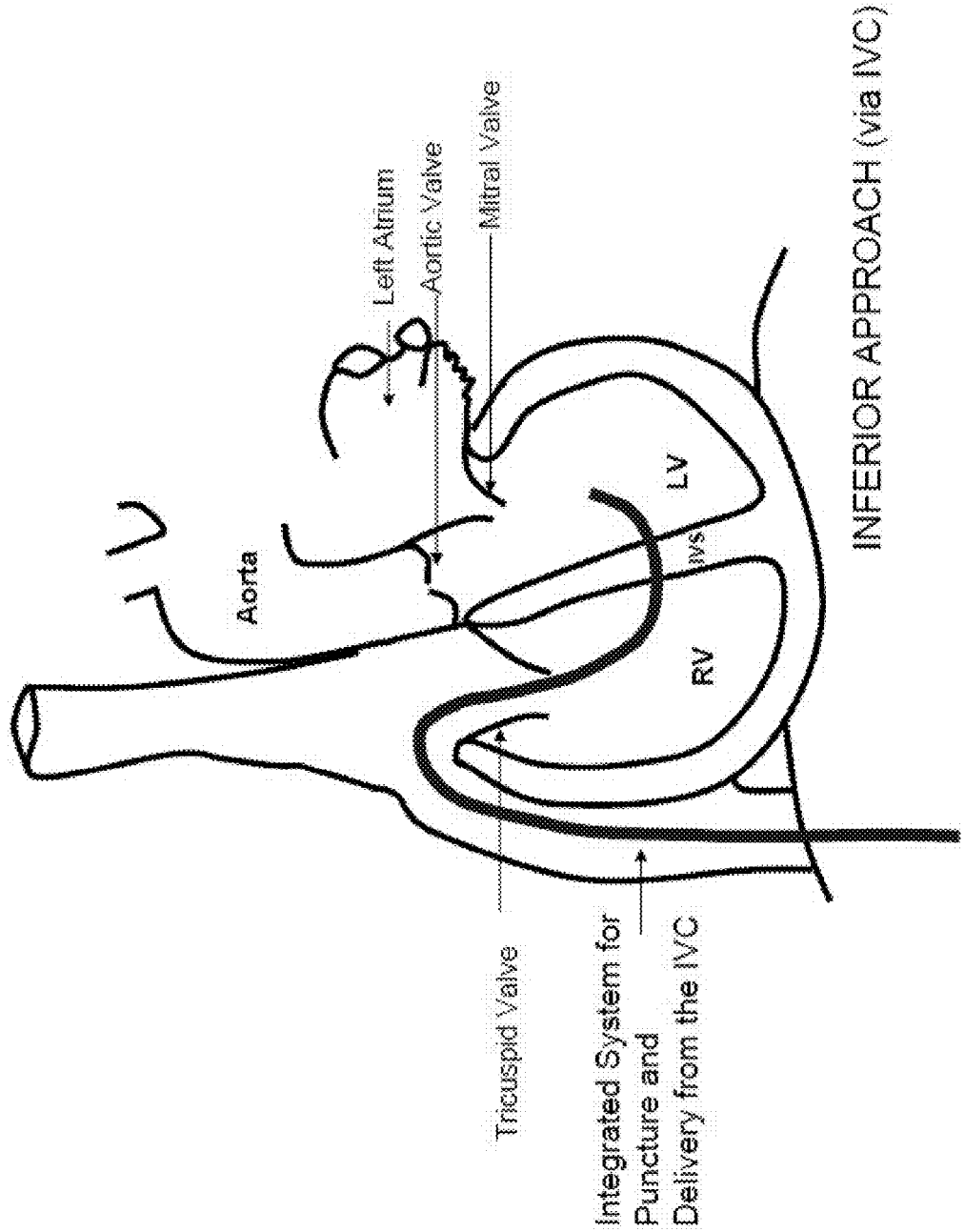
FIG. 5 is a schematic depicting the inter-ventricular transseptal access technique using an inferior approach via the inferior vena cava (IVC).

The method is not limited to any particular access site at which the guidewire and sheath is inserted, or as to any particular route at which the guidewire and sheath is guided. For example, FIG. 4 depicts a superior approach in which a device is guided to the right ventricle via the superior vena cava (SVC). In another embodiment, as depicted in FIG. 5, the method comprises an inferior approach, in which a device is guided to the right ventricle via the inferior vena cava (IVC).

Any standard guidewire and sheath known in the art may be used in the present invention. For example in one embodiment, the guidewire is a J tipped guidewire. In certain embodiments, a primary sheath, for example, a 10 Fr sheath, is guided over the guidewire. The primary sheath can then serve as a passageway for the delivery of a puncture needle and transseptal access sheath to the right ventricle and inter-ventricular septum.

In one embodiment, the method comprises advancing a transseptal access sheath and puncture needle into the right ventricle. In certain embodiments, any standard type or size transseptal access sheath or puncture needle known in the art may be used. Exemplary transseptal access sheaths include, but are not limited to, a Mullins transseptal sheath, braided sheaths, non-braided sheaths, and deflectable sheaths. In certain embodiments, the transseptal access sheath is a sheath/dilator set, as known in the art. The dilator provides for dilation of tissue, and in certain embodiments, is removed after placement of the sheath. In one embodiment, the outer diameter of transseptal access sheath is about 6 Fr to about 32 Fr or more. In one embodiment, the inner diameter of the transseptal access sheath is about 6 Fr to about 32 Fr or more. For example, in certain embodiments, the inner diameter of the transseptal access sheath is appropriate for the passage of standard catheters, probes, or other instrumentation through the inner lumen of the transseptal access sheath. Exemplary puncture needles include, but are not limited to, the Brockenbrough needle (BRK-1), RF needles, and RF wire.

The present method is not limited to any particular puncture location of the inter-ventricular septum. Rather, puncture to provide the transseptal access may be performed any safe and suitable location of the inter-ventricular septum. In certain embodiments, one or more imaging modalities are used to guide the puncture needle and transseptal access sheath to a desired puncture location. For example, in certain embodiments, real-time fluoroscopy, coronary angiography, Intracardiac echocardiography (ICE), or a combination thereof is used to guide the puncture needle and transseptal access sheath to a chosen or desired puncture location. A desired puncture location may be chosen based on numerous factors, including, but not limited to, the lack of major blood vessels, septal thickness, ease of accessing the site, and the like. In certain embodiments, a desired puncture location is stained by injecting an amount of contrast from the puncture needle onto the septum.

The method comprises using the puncture needle to transverse the inter-ventricular septum at the desired puncture location. For example, the puncture needle is inserted through the inter-ventricular septum and into the left ventricle. Entry into the left ventricle may be confirmed using an injection of contrast agent or pressure monitoring. The method then comprises advancing the transseptal access sheath over the puncture needle and into the left ventricle. In certain embodiments, the transseptal access sheath comprises a dilator, which aids in dilating the muscular tissue of the inter-ventricular septum.

Once inter-ventricular transseptal access has been made via the insertion of the transseptal access sheath, the puncture needle, and dilator, if used, may be removed. The transseptal access sheath remains thereby forming a passageway from the right ventricle to the left ventricle. The transseptal access sheath, inserted by way of the present method, can then be used for the guidance of a variety of catheters, probes, or other instrumentation into the left heart for a variety of therapeutic, diagnostic, or interventional procedures. The particular size or type of transseptal access sheath used in the present method may be chosen to allow passage of the appropriate instrumentation necessary to perform the desired therapeutic, diagnostic, or interventional procedure. For example, in one embodiment, the method comprises insertion of an ablation catheter through the transseptal access catheter in order to ablate a region of tissue associated with VT. In another embodiment, the method comprises insertion of catheter through the transseptal access sheath for the delivery of a therapeutic agent to the left heart.

The present invention describes a method of providing safe and effective inter-ventricular transseptal access. This method may be particularly useful in subjects where traditional access via the aorta to the left heart is difficult or dangerous. In such subjects, access to the left heart may comprise surgical procedures, inter-apical access, or access through the pericardium, all of which having the risk to cause damage or excessive bleeding in the subject. In contrast, the present method allows for safe access with minimal bleeding or complications. For example, in certain embodiments, the method has a much lower risk of bleeding and tamponade, given that an epicardial approach to the apex is not required. Damage to major epicardial coronary arteries are also unlikely to occur with the present method. Finally, adhesions of the pericardium in post thoracotomy patients do not pose a challenge.

In certain embodiments, an additional benefit of the inter-ventricular transseptal approach described herein is that the orientation of myocardial fibers at the inter-ventricular septum compared to the apex is better suited for manipulation. The fibers of the left ventricle apex are oriented in a single direction, so that upon removal of large sheaths, spontaneous closure is difficult, resulting in bleeding, and requiring the use of closure devices. On the other hand, given the zig-zag geometry of the fibers of the right ventricle versus the left ventricular at the muscular inter-ventricular septum, crossing at this level would be expected to carry a minimal risk of shunting (Greenbaum et al., 1981, Br Heart J, 45: 248-263; Ho et al., 2008, Eur J Echocardiogr, 10: iii3-7; Pettigrew et al., 1908, Design in Nature, Vol 2; Sanchez-Quintana et al., 1995, Anat Rec, 243: 483-495; Streeter et al., 1969, Circ Res, 24: 339-347). Immediate recoil of the septum occurs and lower trans-myocardial pressure gradients across the right ventricle vs. left ventricle compared to the left ventricle vs. pericardium would decrease the likelihood of bleeding.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1

Percutaneous Inter-ventricular Septal Access in a Patient with Aortic and Mitral Mechanical Valves Described herein is a percutaneous inter-ventricular transseptal puncture technique and placement of a sheath across the inter-ventricular septum for catheter ablation of VT. This method allowed for stable LV access and spontaneous closure of the septal access site.

Patient History

A 35-year-old male was referred for catheter ablation of recurrent VT requiring multiple implantable cardiac defibrillator (ICD) therapies. He had undergone mechanical aortic and mitral valve replacements after developing endocarditis due to a dental abscess. Five years later, he suffered from sudden cardiac arrest and a single-lead ICD was placed. His ejection fraction was estimated at 35% and Q waves were noted on the ECG in the inferior leads. He subsequently suffered from VT storm with increasing number of ICD shocks and anti-tachycardia pace terminated (ATP) episodes despite therapy with sotalol and amiodarone, and also developed trans-aminitis secondary to amiodarone. In the past year, he had suffered from 110 episodes of VT requiring either ATP or ICD shocks and was highly symptomatic, even during the ATP episodes. Given the presence of mechanical prostheses in the mitral and aortic valve positions, a novel method of LV access across the inter-ventricular septum was discussed with the patient, and he agreed to proceed. The patient was asked to continue oral anticoagulation prior to the procedure to avoid mechanical valve thrombosis.

Description of Procedure

Pre-procedure, a cardiac CT angiography was performed to evaluate left ventricular (LV) and right ventricular (RV)

septal anatomy. Trans-esophageal echocardiography prior to the procedure showed no intracardiac shunts, adequate prosthetic valve function, inferior wall motion abnormality, and LVEF of 40%. Noninvasive programmed stimulation prior to start of the procedure reproducibly induced the same monomorphic VT with right bundle branch block morphology, superior axis, and V4 transition with double extra-stimuli.

At the beginning of the procedure, under general anesthesia, venous access was obtained from right internal jugular vein in addition to the right femoral artery and vein and the left femoral vein. Intravenous heparin was started to maintain an activated clotting time above 250 seconds. A right ventriculogram with levophase imaging for left ventriculography was performed to evaluate septal anatomy, positions of prosthetic valves, and LV function. The levophase confirmed a dyskinetic segment of the LV inferior wall, which correlated with inferior Q waves on his baseline ECG. Subsequently, coronary angiography was performed to assess presence of large septal coronary artery perforators at the region of the mid inter-ventricular septum, where safe access could be attempted. Coronary angiography showed no significant coronary artery stenosis and also defined the location of the septal perforator coronary arteries.

Through a 10 F sheath in the right internal jugular vein, an 8.5 French Mullins transseptal sheath was advanced into the RV over a J tipped guide wire. The wire was removed and a Brockenbrough needle (BRK-1) was advanced through the dilator and positioned just inside the distal end of the transseptal sheath. Prior to its insertion, the BRK-1 was manually bent approximately 5 cm from the tip to allow for better reach and contact with the inter-ventricular septum. After insertion of the BRK-1 through the dilator, the dilator tip was pulled back slightly, a counter-clockwise torque was applied, and the sheath was positioned in the mid inter-ventricular septum, above the ICD coil, under fluoroscopic guidance (FIG. 1). This area did not demonstrate any large septal perforator coronary arteries, as confirmed by coronary angiography. Intracardiac echocardiography (ICE) was also used to guide dilator tip position at the interventricular septum. Contrast injection through the BRK-1 needle was used to stain the septum (FIG. 1). It was then easily advanced (without resistance) across the muscular inter-ventricular septum into the LV. Contrast injection and pressure monitoring confirmed position in the LV, FIG. 1. The dilator and sheath were then advanced over the needle and positioned in the LV. The needle and dilator were then removed, the sheath was flushed and a 3.5 mm. ThermoCool ablation catheter (Biosense-Webster, Diamond Bar, Calif.) was advanced via the Mullins sheath into the LV. Additional heparin was given during the procedure to maintain ACT over 300 seconds, and electroanatomic and activation mapping of the LV performed. The procedure from the insertion of the 10 F sheath into the internal jugular vein to the insertion of the transseptal sheath into the LV took approximately 22 minutes. Of note, two other positions, one slightly higher and one slightly lower below the ICD coil were assessed before the final position noted in FIG. 1 was chosen. The position that was finally selected was better seated at the mid-portion of the inter-ventricular septum, which is safer, and allows for easier maneuverability of the sheath within the LV.

Figure 2:
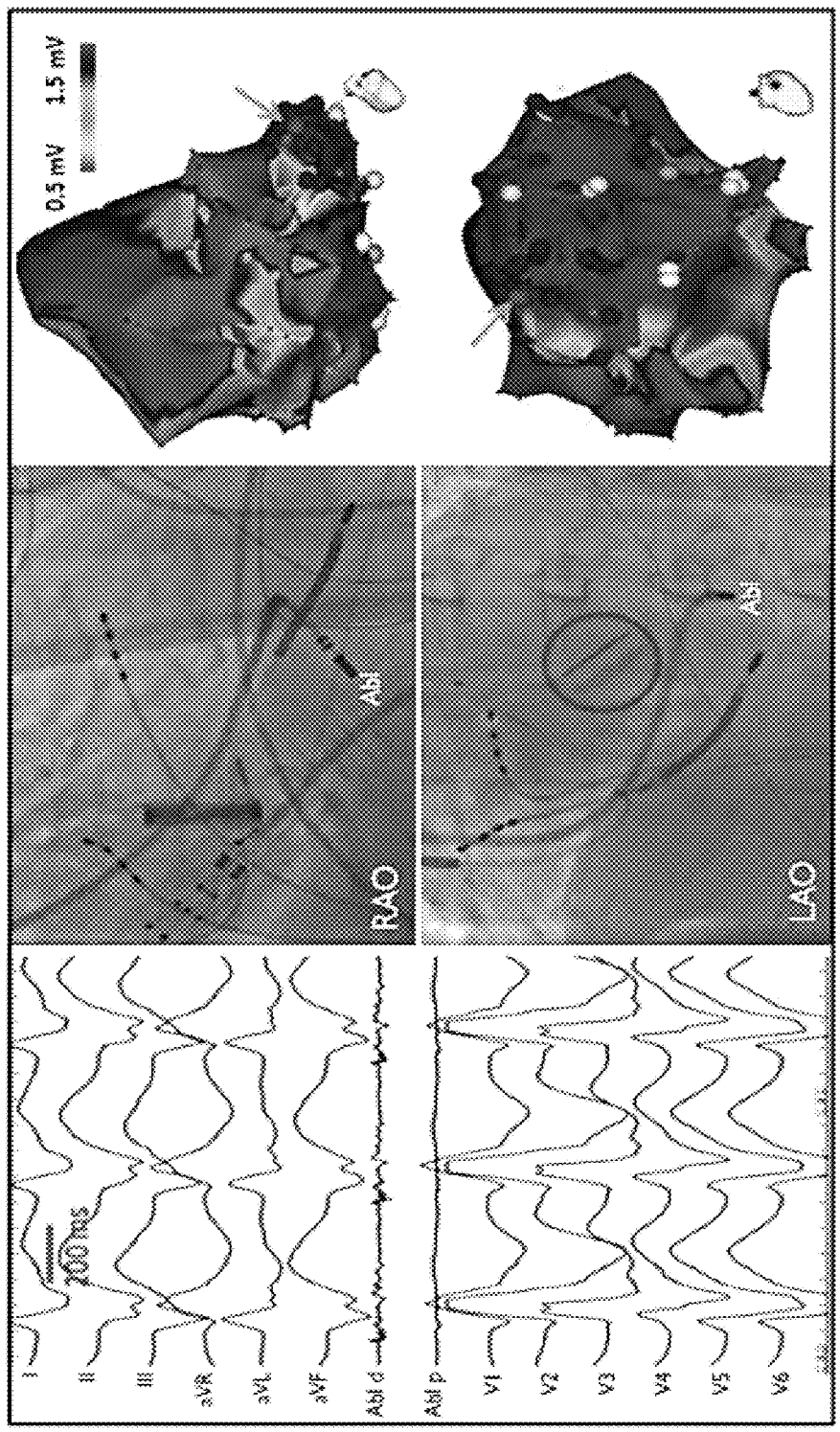
FIG. 2 is a set of images depicting targeted VT, fluoroscopy images and electroanatomic map. The clinical RBBB morphology monomorphic VT with superior axis likely coming from the inferior scar of the LV is shown in the left panel. The successful ablation in the scar is shown in the middle panel and marked on the electroanatomic voltage map (right panel, arrow). Late potentials are further targeted within the inferior scar, as shown by red circles on the electroanatomic map. RAO=right anterior oblique view, LAO=left anterior oblique view, Abl=ablation catheter, Mech MV=mechanical mitral valve. Mech AV=mechanical aortic valve.

The clinical monomorphic VT (FIG. 2), was repeatedly induced and activation mapping of the VT performed. The VT successfully terminated with ablation at an exit site (−56 ms) in the mid inferior wall of the LV, and the acute endpoint of non-inducibility was achieved. Voltage mapping of the inferior wall scar was then performed and all the late potentials that were mapped were targeted with ablation (FIG. 2). At the end of the procedure, the ablation catheter and Mullins sheath were removed from the LV. ICE confirmed lack of pericardial effusion. TEE post procedure showed no evidence of left to right shunt or septal intramural hematoma.

Figure 3:
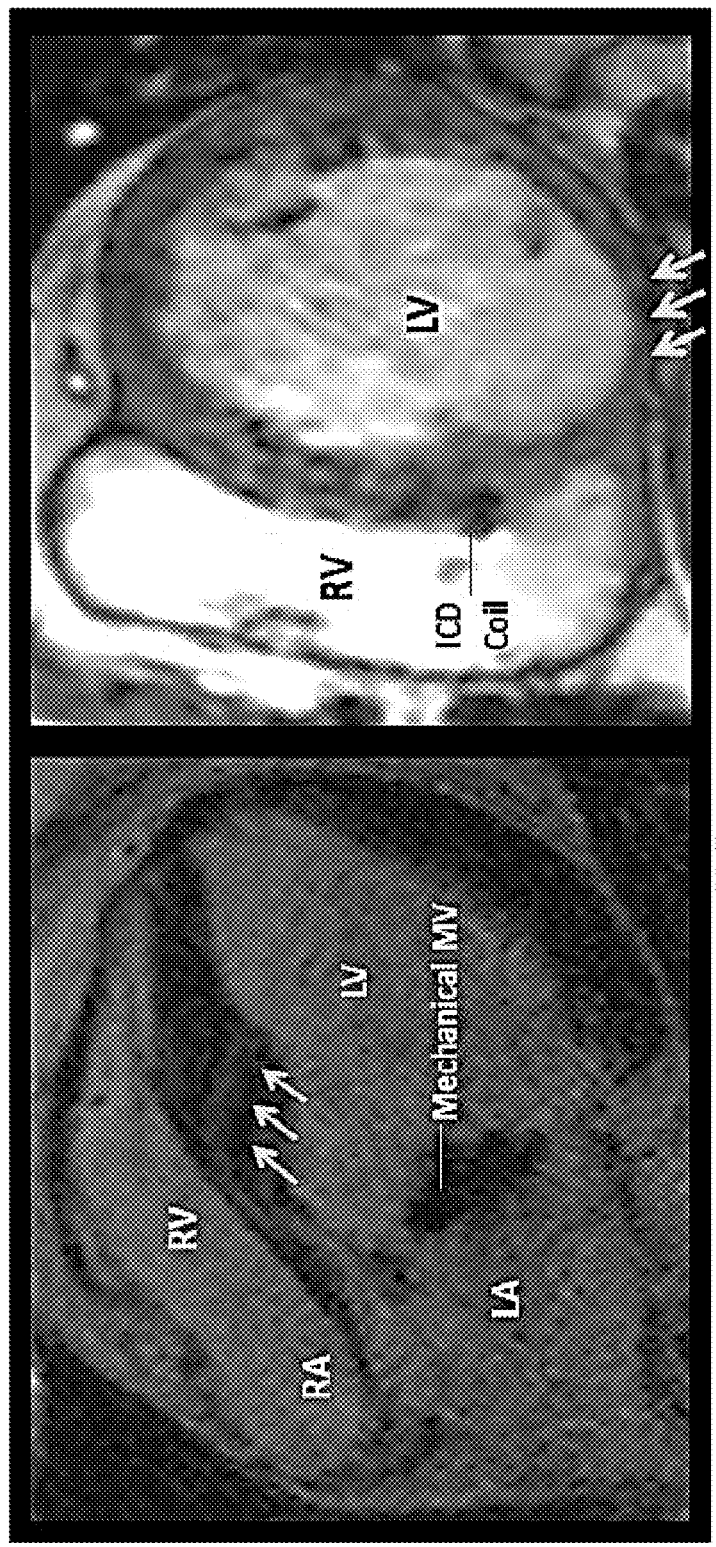
FIG. 3 is a set of images depicting post-procedure magnetic resonance imaging. Magnetic resonance imaging with delayed enhancement (left panel) post procedure shows mild enhancement of the muscular inter-ventricular septum where access to the LV was obtained at a slightly oblique angle (arrows). The right panel shows short-axis bright blood MR imaging, demonstrating lack of a left to right shunt and thinning of the inferior LV wall (arrows). LV=left ventricle, RV=right ventricle, LA=left atrium, RA=right atrium, MV=mitral valve.

Cardiac magnetic resonance imaging (MRI) was also obtained the morning after the procedure to assess location and closure of the transseptal sheath site. The MRI demonstrated a thin linear streak of delayed myocardial enhancement extending across the inter-ventricular septum (FIG. 3), likely representing the path of the transseptal sheath. No evidence of left to right shunt was again noted. Aneurysmal inferior wall dilatation and thinning, noted during ventriculography were also confirmed (FIG. 3).

The patient remained hemodynamically stable throughout the procedure and was discharged home 48 hours later. Repeat transthoracic echocardiography also showed no evidence of a ventricular septal defect and confirmed lack of intracardiac shunt.

In this patient, an endocardial approach was initially chosen, despite the fact that he had normal coronary arteries. An endocardial approach was chosen because he had clear evidence of an inferior wall myocardial infarction with Q waves noted on the inferior leads of his ECG and evidence of focal inferior wall motion abnormality on echocardiography and the levo phase (LV angiogram) of his RV angiography. It was suspected that he suffered from an inferior wall myocardial infarction due to an embolic mechanism that likely occurred during his aortic valve replacement. Therefore, endocardial predominant substrate was suspected and an initial endocardial approach pursued.

The inter-ventricular septum was chosen to be approached from the right internal jugular, instead of the femoral veins. This is because a superior approach would avoid the additional turn required to cross the tricuspid valve, and therefore, would provide an easier route to the inter-ventricular septum. Subsequently, with a simple torque of transseptal sheath and needle, adequate contact on the inter-ventricular septum could be achieved. However, it is noted that the present method is not limited to approaching the septum via the superior approach.

In this patient, no evidence of ventricular septal defect, intramural hematoma, or left to right shunt was found immediately post procedure on ICE, trans-esophageal or trans-thoracic echocardiography, and by MRI. The septal puncture track was faintly seen on contrast enhanced MRI (FIG. 3). In two additional cases (one patient needing LV access across a post-infarct septal defect resulted in a puncture above the defect and another case where this was done intentionally to access the LV for a para-valvular leak closure) where this approach was used the septal puncture site closed spontaneously.

The inter-ventricular transseptal approach described in this report can also be considered for other interventions requiring LV access, where crossing the aortic or mitral valves is undesirable. Currently, in patients with severe aortic stenosis and comorbidities precluding open heart surgery, percutaneous aortic valve replacement using a trans-apical approach has been reported (Huber et al., 2005, J Am Coll Cardiol, 46: 366-370; Ye et al., 2007, Eur J Cardiothorac Surg, 31: 16-21). The inter-ventricular septal approach may present an alternate route for performing these procedures.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of performing a procedure in the left heart of a subject comprising the steps of:
    inserting a puncture needle and transseptal access sheath into the vasculature of the subject;
    advancing the puncture needle and transseptal access sheath into the right ventricle;
    guiding the puncture needle and transseptal access sheath to the inter-ventricular septum;
    advancing the puncture needle through the inter-ventricular septum into the left ventricle;
    advancing at least a portion of the transseptal access sheath over the puncture needle into the left ventricle;
    removing the puncture needle such that the transseptal access sheath remains positioned across the inter-ventricular septum, thereby forming a passageway from the right ventricle to the left ventricle through the transseptal access sheath;
    advancing an instrument through the transseptal access sheath into the left ventricle;
    performing a procedure in the left ventricle with the instrument while the transseptal access sheath is maintained across the inter-ventricular septum; and
    removing the instrument through the transseptal access sheath.

2. The method of claim 1, wherein the puncture needle and transseptal access sheath are advanced into the right ventricle via the superior vena cava.

3. The method of claim 1, wherein the puncture needle and transseptal access sheath are advanced into the right ventricle via the inferior vena cava.

4. The method of claim 1, wherein the puncture needle and transseptal access sheath are advanced into the right ventricle within a primary sheath guided to the right ventricle.

5. The method of claim 1, comprising determining a location on the inter-ventricular septum where the puncture needle and transseptal access sheath is to be guided.

6. The method of claim 5, wherein determining the location on the inter-ventricular septum comprises the use of a procedure selected from the group consisting of real-time fluoroscopy, coronary angiography, Intracardiac echocardiography (ICE), and a combination thereof.

7. The method of claim 1, wherein the instrument is selected from the group consisting of therapeutic catheters, imaging catheters, probes, and surgical instrumentation, into the left heart.

8. The method of claim 1, wherein the procedure comprises a treatment of a condition or defect in the left heart.

9. The method of claim 1, wherein the procedure comprises diagnosing a condition or defect in the left heart.

10. The method of claim 1, wherein the method is used to guide an ablation catheter into the left heart through the passageway formed by the transseptal access sheath for treatment of ventricular tachycardia.

* * * * *